United States Patent
Azzaro et al.

(10) Patent No.: US 7,612,681 B2
(45) Date of Patent: Nov. 3, 2009

(54) SYSTEM AND METHOD FOR PREDICTING FALL RISK FOR A RESIDENT

(75) Inventors: Steven Hector Azzaro, Schenectady, NY (US); Mark Mitchell Kornfein, Latham, NY (US); Vrinda Rajiv, Schenectady, NY (US); Hunt Adams Sutherland, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 319 days.

(21) Appl. No.: 11/671,770

(22) Filed: Feb. 6, 2007

(65) Prior Publication Data

US 2008/0186189 A1    Aug. 7, 2008

(51) Int. Cl.
*G08B 23/00* (2006.01)

(52) U.S. Cl. .................. 340/573.4; 340/573.1; 600/595

(58) Field of Classification Search .............. 340/573.1, 340/573.7, 573.4, 686.1, 541, 551, 552, 561, 340/565, 539.22, 539.26, 506, 825.19, 523, 340/526, 529; 600/595; 702/141, 160
See application file for complete search history.

(56) References Cited

U.S. PATENT DOCUMENTS

| | | | | |
|---|---|---|---|---|
| 5,937,443 | A * | 8/1999 | Kageyama et al. | 2/69 |
| 7,150,048 | B2 * | 12/2006 | Buckman | 2/465 |
| 7,154,399 | B2 | 12/2006 | Cuddihy et al. | |
| 2005/0237179 | A1 | 10/2005 | Cuddihy et al. | |
| 2006/0001545 | A1 | 1/2006 | Wolf | |
| 2006/0055543 | A1 | 3/2006 | Ganesh et al. | |
| 2006/0058704 | A1 | 3/2006 | Graichen et al. | |
| 2006/0089538 | A1 | 4/2006 | Cuddihy et al. | |
| 2006/0145874 | A1 | 7/2006 | Fredriksson et al. | |
| 2006/0195050 | A1 * | 8/2006 | Alwan et al. | 600/595 |

FOREIGN PATENT DOCUMENTS

| | | |
|---|---|---|
| EP | 877346 A1 | 11/1998 |
| EP | 1195139 | 4/2002 |
| WO | 03065891 A2 | 8/2003 |
| WO | WO2004047039 | 6/2004 |

OTHER PUBLICATIONS

Close, J.C.T., R. Hooper, E. Glucksman, S.H.D. Jackson and C.G. Swift, "Predictors of falls in a high risk population: results from the prevention of falls in the elderly trial (PROFET)", Journal of Emerg. Med, 2003; 20; pp. 421-425.

(Continued)

*Primary Examiner*—Toan N Pham
(74) *Attorney, Agent, or Firm*—Jenifer E. Haeckl

(57) ABSTRACT

A system for predicting fall risk for a resident is provided. The system includes a fall risk prediction subsystem, configured to predict a fall risk likelihood for a resident based on data measurements collected from one or more sensors. One or more of the sensors comprise range control radar (RCR) sensors. The fall risk prediction subsystem further includes a fall analysis component configured to analyze the data measurements from one or more of the sensors and a fall risk assessment component configured to predict the fall risk likelihood for the resident based on the analysis.

34 Claims, 4 Drawing Sheets

OTHER PUBLICATIONS

Newton, Roberta A., Ph.D., "Heros: Reducing Falls and Serious Injuries", Training Program Manual, Jun. 2004, pp. 1-55.

Curry, R.G., M.D., Mrs. M. Trejo Tinoco and Mr. D. Wardle, "Telecare: Using Information and Communication Technology to Support Independent Living by Older, Disabled and Vulnerable People", Jul. 2003, pp. 1-50.

U.S. Appl. No. 11/164,577, filed Nov. 29, 2005, pending.

* cited by examiner

SYSTEM AND METHOD FOR PREDICTING FALL RISK FOR A RESIDENT

BACKGROUND

The invention relates generally to home monitoring systems and more particularly to a system and method for predicting the likelihood of fall of a resident in a home.

Many elderly people are at risk from a variety of hazards, such as falling, tripping, or illness. For example, health statistics and studies show that falling is a major problem among the elderly. The risk of falling increases with age, such that, studies suggest that about 32% of individuals above 65 years of age and 51% of individuals above 85 years of age fall at least once a year. In addition, many elderly people live alone. Therefore, the elderly are at additional risk that they may not be able to call for help or receive assistance in a timely manner after experiencing a fall or illness.

As a result, systems that enable a resident of a home to call for assistance from anywhere in a home have been developed. In systems such as the Personal Emergency Response Systems (PERS), the elderly or disabled individual wears a watch, pendent or other like device and presses a button in the event of an emergency, such as a fall. The depressed button enables an alarm signal to be automatically sent to a central monitoring facility, when the resident has fallen. A disadvantage of using these devices is that they have to be worn by the person in order to work and are useless if the person is not wearing them. Furthermore, these devices provide means to get help only after a fall has occurred. Thus, there is a risk that in an emergency situation, the resident may not receive proper assistance in a timely manner.

Certain systems rely on motion sensors to try to identify when a person has fallen. There may be extended periods where a resident is not moving for reasons other than the person having fallen or becoming incapacitated, such as watching television from a chair or sleeping in bed. Systems that rely on motion sensors require the person to be motionless for a considerable amount of time before the system is able to conclude that the resident has fallen or become incapacitated, as opposed to exhibiting normal inactive behavior.

Fall prevention screening techniques have also been used to identify a person's likelihood of falling. These techniques are traditionally performed through manual tests given by a trained professional, who determines the likelihood of fall risk for a person by identifying a set of typical fall risk factors that affect the person. A fall risk screening form is generally presented to the person that lists a set of possible fall risk factors for the person, and serves as a mechanism for the person to have these risk factors assessed by his/her therapist. A disadvantage with using fall risk screening techniques is that they are performed using manual tests that are only conducted periodically, such as for example, on a monthly basis. In addition, these techniques cannot be used to accurately predict future falls.

It would be desirable to develop a technique that enables the frequent monitoring of data and factors that increase the likelihood of falling of a resident in a home, in real time. In addition, it would also be desirable to develop a system and method for automatically predicting the likelihood of fall for a resident in a home.

BRIEF DESCRIPTION

In one embodiment, a system for predicting fall risk for a resident is provided. The system comprises one or more sensors configured to collect data measurements related to an activity of a resident. One or more of the sensors are configured to measure one or more motion characteristics related to the resident. The system further comprises a fall risk prediction subsystem, configured to predict a fall risk likelihood for the resident based on the data measurements collected from one or more of the sensors.

In a second embodiment, a system for predicting fall risk for a resident is provided. The system comprises a fall risk prediction subsystem, configured to predict a fall risk likelihood for a resident based on data measurements collected from one or more sensors. One or more of the sensors comprise range control radar (RCR) sensors. The fall risk prediction subsystem further comprises a fall analysis component configured to analyze the data measurements from one or more of the sensors and a fall risk assessment component configured to predict the fall risk likelihood for the resident based on the analysis.

In a third embodiment, a method for predicting fall risk for a resident is provided. The method comprises the steps of collecting data measurements related to an activity of a resident using one or more sensors positioned within a home of the resident. One or more of the sensors comprise range control radar (RCR) sensors. The method further comprises the step of predicting the fall risk likelihood for the resident based on the data measurements collected from one or more of the sensors.

DRAWINGS

These and other features, aspects, and advantages of the present invention will become better understood when the following detailed description is read with reference to the accompanying drawings in which like characters represent like parts throughout the drawings, wherein.

Figure 3:
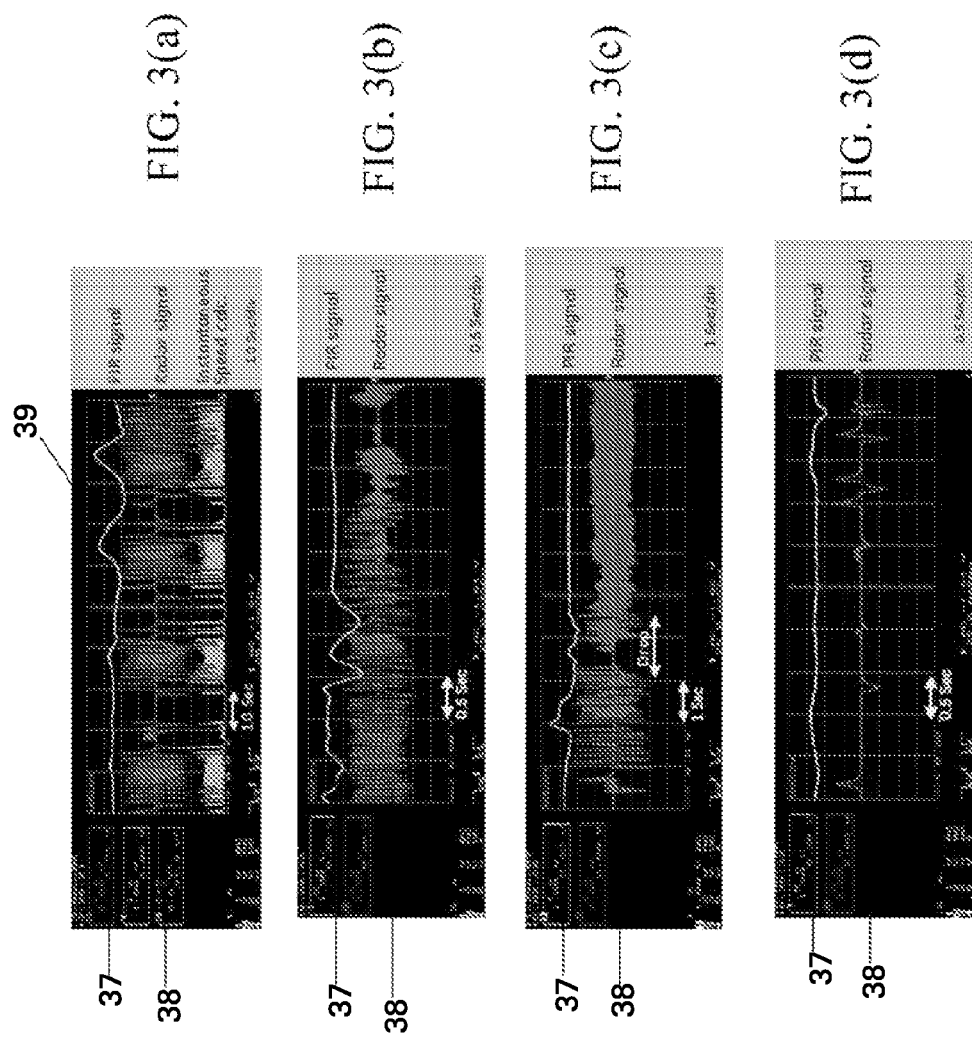
Figure 4:
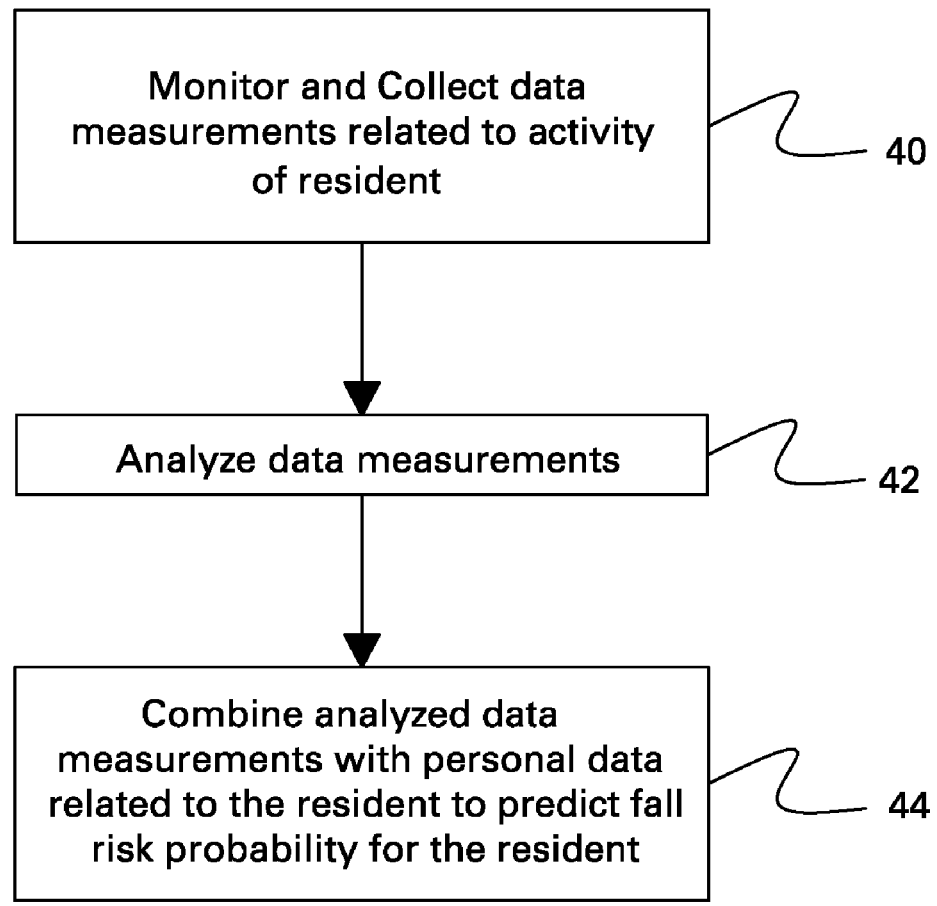

FIGS. 3(*a*)-3(*d*) represent plots illustrating raw signal data obtained from one or more of the sensors positioned within the home of the resident for the detection of one or more motion characteristics related to the resident; and FIG. 4 illustrates one or more process steps that may be used in the systems and methods for predicting fall risk for a resident in a home.

DETAILED DESCRIPTION

Figure 1:
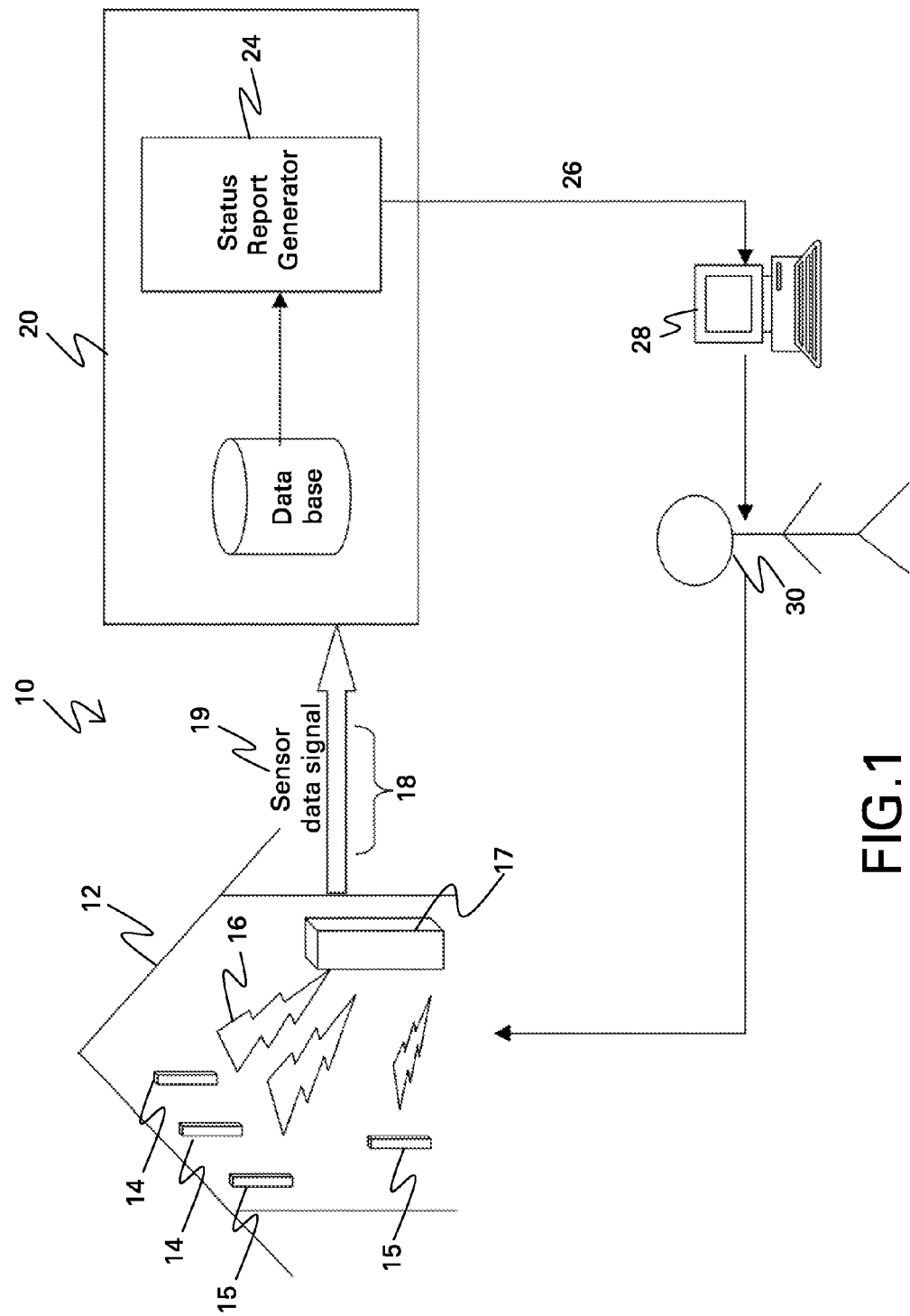
FIG. 1 is a schematic view of a system for predicting fall risk for a resident in a home, in accordance with one embodiment of the invention.

FIG. 1 is a schematic view of a system for predicting fall risk for a resident in a home, in accordance with one embodiment of the invention. As shown in FIG. 1, the system 10 generally comprises one or more range controlled radar (RCR) sensors 14, a communications relay panel 17 and a fall risk prediction subsystem 20. The system 10 may further include one or more sensors 15, such as, but not limited to, motion sensors and location sensors positioned at various locations within a home 12 of a resident, to identify movement, location or activity of the resident. The motion sensors may be any of a variety of different types of motion sensors, such as, for example, passive infrared sensors, ultrasound sensors, microwave sensors and infrared sensors. The location sensors detect a specific location of the resident within the home 12 and provide signals when the resident is located at the specific location within the home. The location sensors may include, but are not limited to, pressure pad sensors, infrared sensors, and other sensors that can detect when the resident is located at specific locations within the home 12, such as when the resident is in bed, sitting on a couch or a chair, or when located at some other specific location. The motion sensors provide data regarding specific activities of the resident within the home 12. In addition, the system 10 may also comprise other suitable sensors such as photometers, pressure sensors, hazard sensors and security sensors.

In one embodiment, the sensors 14, 15 are configured to measure one or more motion characteristics related to the resident. In particular, the sensors 14, 15 are configured to convert the movement of the resident within an area or a field of view within the home 12 into signals that measure one or more motion characteristics related to the resident. In one embodiment, the RCR sensors 14 are configured to monitor and collect data measurements related to an activity of the resident. The RCR sensors 14 may include, but are not limited to range gated radar sensors and microwave impulse radar sensors. In a particular embodiment, the RCR sensors 14 measure one or more motion characteristics, including one or more walking features related to the resident. The walking features may include, but are not limited to, gait speed, gait length, variable movement speed, gait/balance instability, transit pauses and drop attacks related to the resident.

In an exemplary operation of the system 10, the RCR sensors 14 measure the actual speed and changes in speed of movement of the resident as he/she moves within an area in the home 12, by producing frequency signals that vary in proportion to the speed of movement of the resident. In one embodiment, the RCR sensors 14 measure specific attributes related to gait/balance instability for the resident by transmitting radar signals to the resident within a coverage area and calculating his/her size and distance from the RCR sensors. In another embodiment, the RCR sensors 14 measure variable movement speed for a resident, by measuring the time required for the resident to cross an area within the home 12. In yet another embodiment, the RCR sensors 15 measure transit pauses for a resident by monitoring pauses that are different from the typical pauses for a resident, and measuring incremental changes in transit. The RCR sensors 14 may also be used to measure extended pauses during transit, by monitoring pauses that are much longer than typical pauses for a resident, and measuring incremental changes in transit. The RCR sensors 14 may also measure sudden drop attacks, indicating a fall of a resident. As used herein, a "drop attack" refers to a sudden or spontaneous fall while standing or walking, with complete recovery in seconds or minutes.

Referring to FIG. 1, the sensors 15 may be further configured to collect data measurements related to environmental risk factors and intrinsic risk factors related to the resident. As used herein, an "environmental risk factor" may include, but is not limited to, lighting, support surface structure and other obstacles present in the home 12 of the resident and an "intrinsic risk factor" may include, but is not limited to, cognitive impairment, postural hypotension and visual impairment related to the resident. In one embodiment, a motion sensor may be used in conjunction with a photometer to detect situations where a resident is moving through a poorly lit area in the home 12 of the resident. In another embodiment, the sensors 15 may be used to obtain data measurements that relate to specific patterns of movement of the resident by measuring path and time consistency of a resident's movement in an area. The sensors 15 may also be used to monitor changes in the blood pressure for a resident leading to postural hypotension, in real time, using devices such as wireless blood pressure devices and pressure pads. The sensors 15 may also be used to monitor visual impairment or declining vision for a resident, in real time, by measuring normal TV viewing distances for a resident, using one or more proximity measures.

The sensors 14, 15 may be wireless sensors capable of wirelessly communicating signals 16, which include measurement data collected, to the communications relay panel 17. It should be appreciated, however, that the sensors 14, 15, may instead be sensors hardwired to the communications relay panel 17. The communications relay panel 17 then communicates the sensor data measurements from the sensors 14, 15 by sending a data signal 19 containing the data measurements to the fall risk prediction subsystem 20 by way of a suitable wired or wireless communication platform 18, such as, for example, wired telephone, wireless telephone, two-way walkie-talkie, pager, cable, the Internet, or any other wireless communication platform. Depending upon the communication platform 18 chosen, the data signals 19 may be sent in near real-time or may be sent at discrete, irregular intervals. As used herein, "sensor data measurements" may include sensor information, such as, but not limited to, data collected by one or more sensors and one or more activities detected.

The fall risk prediction subsystem 20, which may be remote from the home 12, generally comprises a database 22, and a status report generator 24. The fall risk prediction subsystem 20 is configured to predict a fall risk likelihood for the resident based on the data measurements collected from one or more of the sensors 14, 15. The database 22 serves as a collection vessel for the sensor data measurements communicated via the data signals 19. The database 22 is also configured to store the data measurements analyzed by the fall risk prediction subsystem 20, as will be described in greater detail below. Upon a request from the caregiver 30 for a status report, the analyzed data measurements may be forwarded from the database 22 to the status report generator 24. The status report generator 24 may communicate a near real-time status signal 26 to a personal computer 28 of the caregiver 30. As used herein, "near real-time" refers to a range of almost instantaneously to up to three minutes. For example, for a two-way page communication platform 18, the amount of time required for the communication can be between two and three minutes. The status report generator 24 may be programmed to update the report for each home 12 at a certain interval, such as, for example, every ten minutes. The status signal 26 may include a report generated by the status report generator 24. The format and substance of the report may be dependent upon the request of the caregiver 30. It should be appreciated that the signal 26 can instead be communicated via a personal digital assistant (PDA), a pager, a facsimile machine, a cable, or a telephone or voice mail account instead of via the personal computer 28.

Figure 2:
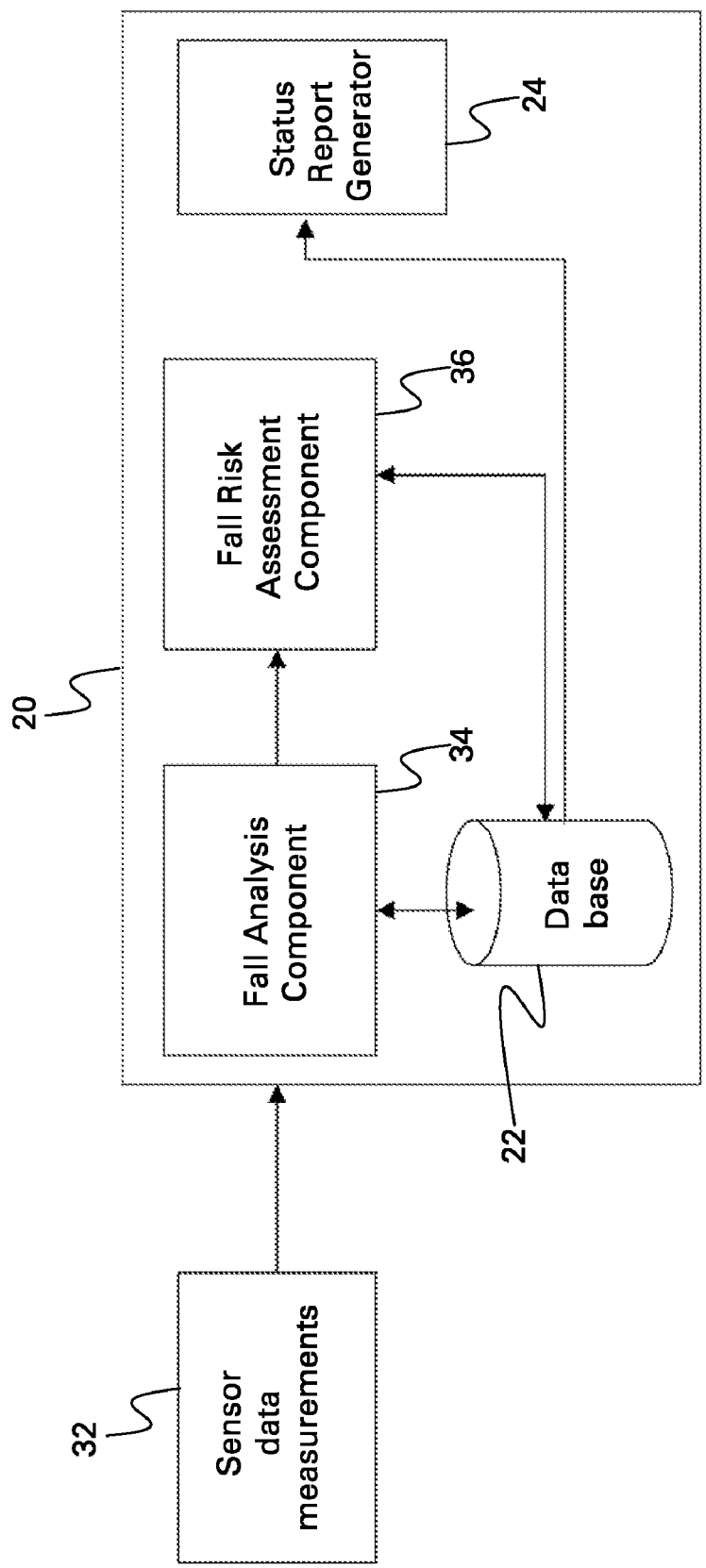
FIG. 2 is a detailed view of the fall risk prediction subsystem illustrated in FIG. 1.

FIG. 2 is a detailed view of the fall risk prediction subsystem illustrated in FIG. 1. As shown in FIG. 2, the fall risk prediction subsystem 20 comprises a fall analysis component 34, a fall risk assessment component 36, a database 22 and a status report generator 24. In one embodiment, the fall risk prediction subsystem 20 is configured to predict a fall risk likelihood for a resident based on data measurements collected from one or more of the sensors 14, 15. In a particular embodiment, the fall analysis component 34 may be configured to analyze the data measurements 32, from the sensors 14, 15. For example, the fall analysis component 34 may analyze the walking features related to the resident, based on the data measurements from the sensors 14, 15. In particular, the fall analysis component 34 may analyze the data measurements from the sensors 14, 15 to determine trends suggestive of an increase in transit time for a resident, or trends suggestive of repeated movements of a resident in a dark room, incremental trend changes indicating poor balance or gait issues and decreased or abrupt changes in uniformity in the movement of the resident, indicating confusion or cognitive impairment for the resident.

The fall analysis component 34 may further be configured to interpret and analyze the data measurements 32, from the sensors 14, 15 using one or more risk measures. These risk measures may include, but are not limited to, quantitative fall risk measures for a resident, such as, for example, gait speed, timed up and go, functional reach, gait index and balance scales. The base line for such risk measures may be derived from general population data or from data gathered on a given resident or patient. "As examples, gait speed" may be predefined for a given embodiment as a measure of a person's normal walking speed over a predetermined distance, such as twenty feet. "Timed up and go" may measure the time that is takes a person to stand up from an arm chair, walk three meters, turn around, walk back to the chair and sit down. "Functional reach" may measure the distance a person can reach forward without loosing his or her balance. "Gait index" may measure the ability of a person to adapt gait to changes in task demands and "balance scales" may measure the ability of a person to maintain balance while performing normal activities.

The fall risk assessment component 36 is configured to combine the analyzed data measurements from the fall analysis component 34 with personal data related to the resident to predict the fall risk likelihood for the resident. In one embodiment, the personal data may include, but is not limited to, fall history, medication and medical conditions related to the resident. Fall history may include, for example, information on frequency of falls, location of previous falls, and activity during falls for the resident. Medications may include the number of medications, changes in medication and medication compliance related to the resident. Medical conditions may include up to date information on the diagnosis of long-term afflictions and short-term illnesses for the resident.

The fall risk assessment component 36 may further use one or more computational or statistical techniques to predict the fall risk likelihood for the resident. In one embodiment, a Hidden Markov Model (HMM) is used to predict the fall risk likelihood. In a particular embodiment, the HMM is used to distinguish among a normal walk, a limp, or a shuffle for a resident using wavelet analysis. In another embodiment, a Bayesian network is used to predict the fall risk likelihood. A Bayesian network is a probabilistic-based inference methodology for reasoning under uncertainty. Bayesian networks may be used to model a causal relationship among system variables for system state estimation, given a classification system. Information is inserted into the Bayesian network through evidence nodes and probability propagation is performed to obtain updated belief assessments, or probabilities.

In a particular embodiment, a Bayesian network is used to determine a gait type for a person, such as, for example, walking or shuffling, by providing a posterior belief in each of a possible set of classes. The Bayesian network may be expressed as a two class, two-component mixture model indicating a posterior belief in each of the possible classes, corresponding to a particular gait type for the person. The Bayesian network may also be utilized in a decision making process. For example, prior gait classification information may be augmented with additional situational, behavioral and personal information to predict the fall risk likelihood for the resident.

The database 22 is configured to store the analyzed data measurements from the fall analysis component 34 and the fall risk assessment component 36. The status report generator 24 may be configured to generate alerts or reports that request immediate help, for use by the caregiver 30 (shown in FIG. 1) or medical personnel. As mentioned above, the format and substance of the report may be dependent upon the request of the caregiver 30.

FIGS. 3(a)-3(d) represent plots illustrating raw signal data obtained from one or more of the sensors positioned within the home of the resident for the detection of one or more motion characteristics related to the resident.

FIG. 3(a) is a plot illustrating raw signal data obtained from one or more of the sensors to detect a halting gait associated with the resident. In the example plot shown in FIG. 3(a), a radar signal 38 generated using one or more of the RCR sensors 14 along with a PIR signal 37 generated using one or more of the sensors 15 may be used to record movement and some gaps where there is little movement from the resident. As may be observed from the plot shown in FIG. 3(a), the PIR signal 37 registers entry into new locations as indicated by the peaks 39 in the signal. The sensors 14, 15 measure changes in speed of movement, without regard to direction, as the resident walks across an area within the home 12, enabling the computation of the actual speed of movement of the resident, across an area within the home 12.

FIG. 3(b) is a plot illustrating raw sensor data obtained from one or more of the sensors to detect an event in which the resident walks across an area in a steady pace and sits down in a chair. As may be observed from the plot shown in FIG. 3(b), the signals 37, 38 from the sensors 14, 15 indicate relatively steady movement until the resident sits down.

FIG. 3(c) is a plot illustrating raw sensor data obtained from one or more of the sensors to detect a fall event, in which the resident drops to the floor.

FIG. 3(d) is a plot illustrating raw sensor data obtained from one or more of the sensors to detect a stationary position of the resident in a chair, where the resident makes small arm motions in the chair.

FIG. 4 illustrates one or more process steps that may be used in the systems and methods for predicting a fall risk for a resident in a home. In step 40, data measurements, related to an activity of a resident, are monitored and collected using one or more sensors 14, 15 (shown in FIG. 1) positioned within the home 12 (shown in FIG. 1) of the resident. The sensors include, but are not limited to, range control radar sensors, motion sensors, photometers, pressure sensors and location sensors. Step 40 also may comprise the steps of monitoring and collecting data measurements related to one or more environmental risk factors and/or one or more intrinsic risk factors related to the resident or the resident's living area. Step 40 further comprises the step of measuring one or more walking features related to the resident based on the collected data measurements. The walking features may include, but are not limited to, gait speed, gait length, variable movement speed, gait/balance instability, transit pauses and drop attacks.

In step 42, the data measurements are analyzed. As mentioned above, one or more walking features may be analyzed, based on the data measurements from the sensors 14, 15. The data measurements may also be analyzed to determine trends suggestive of an increase in transit time for a resident, incremental trend changes indicating poor balance or gait issues and decreased or abrupt changes in uniformity in the movement of the resident, indicating confusion or cognitive impairment for the resident.

In step 44, the analyzed data measurements are combined with personal data related to the resident to predict the fall risk likelihood for the resident. Personal data may include, but is not limited to, fall history, medication and medical conditions related to the resident. As mentioned above, one or more computational or statistical techniques may further be applied on the analyzed data measurements to predict the fall risk likelihood for the resident.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for predicting fall risk for a resident, the system comprising:
   one or more sensors configured to collect data measurements related to an activity of a resident, wherein one or more of the sensors are configured to measure one or more motion characteristics related to the resident, wherein one or more of the sensors comprise range controlled radar (RCR) sensors, wherein at least one of the RCR sensors measure one or more walking features based on the collected data measurements, wherein one or more of the walking features is selected from a group consisting of: gait length, variable movement speed, gait/balance instability, transit pauses and drop attacks; and
   a fall risk prediction subsystem, configured to predict a fall risk likelihood for the resident based on the data measurements collected from one or more of the sensors.

2. The system of claim 1, wherein the range controlled radar (RCR) sensors comprise one of range gated radar sensors and microwave impulse radar sensors.

3. The system of claim 1, wherein one or more of the sensors further comprises one or more sensors selected from a group consisting of: motion sensors, photometers, pressure sensors and location sensors positioned within a home of the resident.

4. The system of claim 3, wherein one or more of the sensors are configured to collect data measurements related to at least one of an environmental risk factor and an intrinsic risk factor.

5. The system of claim 4, wherein one or more of the environmental or intrinsic risk factors is related to the resident.

6. The system of claim 4, wherein one or more of the environmental risk factors is selected from a group consisting of: lighting, support surface structure and obstacles present in a living area of the resident.

7. The system of claim 4, wherein one or more of the intrinsic risk factors is selected from a group consisting of: cognitive impairment, postural hypotension and visual impairment.

8. The system of claim 1, wherein the fall risk prediction subsystem is configured to analyze the data measurements from one or more of the sensors.

9. The system of claim 8, wherein the fall risk prediction subsystem is further configured to combine the analyzed data measurements with personal data related to the resident to predict the fall risk likelihood for the resident.

10. The system of claim 9, further comprising a database configured to store the analyzed data measurements.

11. The system of claim 9, wherein at least a portion of the personal data is selected from a group consisting of: fall history, medication and medical conditions related to the resident.

12. The system of claim 9, wherein the fall risk prediction subsystem uses one or more computational and statistical techniques to predict the fall risk likelihood for the resident.

13. The system of claim 1, further comprising a status report generator configured to generate a near real time status report related to the fall risk likelihood of the resident.

14. A system for predicting fall risk for a resident, the system comprising:
   a fall risk prediction subsystem, configured to predict a fall risk likelihood for a resident based on data measurements collected from one or more sensors, wherein one or more of the sensors comprise range control radar (RCR) sensors, wherein at least one of the RCR sensors is configured to measure one of gait length, variable movement speed, gait/balance instability, transit pauses and drop attacks, and wherein the fall risk prediction subsystem further comprises:
   a fall analysis component configured to analyze the data measurements from one or more of the sensors; and
   a fall risk assessment component configured to predict the fall risk likelihood for the resident based on the analysis.

15. The system of claim 14, wherein one or more of the sensors further comprises one or more sensors selected from a group consisting of: motion sensors, photometers, pressure sensors and location sensors positioned within a home of the resident.

16. The system of claim 15, wherein one or more of the sensors are configured to collect data measurements related to at least one of an environmental risk factor and an intrinsic risk factor.

17. The system of claim 16, wherein one or more of the environmental or intrinsic risk factors is related to the resident.

18. The system of claim 14, wherein at least one of the RCR sensors comprises one of a range gated radar sensor and microwave impulse radar sensor.

19. The system of claim 14, wherein the fall analysis component is configured to analyze one or more of the walking features related to the resident, based on the data measurements.

20. The system of claim 19, wherein the fall risk assessment component is further configured to combine the analyzed data measurements with personal data related to the resident to predict the fall risk likelihood for the resident.

21. The system of claim 20, wherein the fall risk assessment component uses one or more computational and statistical techniques to predict the fall risk likelihood for the resident.

22. The system of claim 14, further comprising a database configured to store the analyzed data measurements.

23. The system of claim 14, further comprising a status report generator configured to generate a near real time status report related to the fall risk likelihood of the resident.

24. A method for predicting fall risk for a resident, the method comprising:
   collecting data measurements related to an activity of a resident using one or more sensors positioned within a home of the resident, wherein one or more of the sensors comprises one or more range control radar (RCR) sensors, wherein at least one of the RCR sensors is configured to measure one of gait/balance instability, transit pauses and drop attacks; and
   predicting a fall risk likelihood for the resident based on the data measurements collected from one or more of the sensors.

25. The method of claim 24, wherein one or more of the sensors further comprises one or more sensors selected from a group consisting of: motion sensors, photometers, pressure sensors and location sensors positioned within a home of the resident.

26. The method of claim 25, wherein one or more of the sensors are configured to collect data measurements related to at least one of an environmental risk factor and an intrinsic risk factor.

27. The method of claim 26, wherein one or more of the environmental risk factors is selected from a group consisting of: lighting, support surface structure and obstacles present in a living area of the resident.

28. The method of claim 26, wherein one or more of the intrinsic risk factors is selected from a group consisting of: cognitive impairment, postural hypotension and visual impairment.

29. The method of claim 24, wherein at least one of the RCR sensors comprises a microwave impulse radar sensor.

30. The method of claim 24, further comprising analyzing the data measurements to predict the fall risk likelihood for the resident.

31. The method of claim 30, further comprising combining the analyzed data measurements with personal data related to the resident to predict the fall risk likelihood for the resident.

32. The system of claim 31, wherein at least a portion of the personal data is selected from a group consisting of: fall history, medication and medical conditions related to the resident.

33. The method of claim 31, comprising storing the analyzed data measurements.

34. The method of claim 31, comprising using one or more computational and statistical techniques to predict the fall risk likelihood for the resident. and statistical techniques to predict the fall risk likelihood for the resident.

* * * * *